| United States Patent [19] | [11] Patent Number: 4,783,334 |
|---|---|
| Ikushima | [45] Date of Patent: Nov. 8, 1988 |

[54] STABLE SOLID PREPARATION OF THIOL ESTER DERIVATIVE

[75] Inventor: Heiji Ikushima, Saitama, Japan

[73] Assignee: Chugai Seiyaku Kabushiki Kaisha, Tokyo, Japan

[21] Appl. No.: 4,144

[22] Filed: Jan. 16, 1987

[30] Foreign Application Priority Data

Jan. 21, 1986 [JP]  Japan .................................. 61-10706
Jun. 2, 1986 [JP]  Japan ................................ 61-125901

[51] Int. Cl.$^4$ ..................... A61U 31/40; A61U 31/79; A61U 33/20
[52] U.S. Cl. ..................................... 424/78; 424/149; 514/408
[58] Field of Search .................. 560/19; 562/433, 427; 514/79, 960, 970, 408; 426/23; 424/465, 501, 78, 149

[56] References Cited

U.S. PATENT DOCUMENTS 4,283,407  8/1981  Malen .

FOREIGN PATENT DOCUMENTS 507575  11/1975  Australia .
0072868  3/1983  European Pat. Off. .
2355743  8/1973  Fed. Rep. of Germany .
2508040  6/1982  France .
656535  9/1986  Switzerland .

OTHER PUBLICATIONS

Tanaka, S; Kuromaru, K; Fujimura, Y; Matsunaga, S; Iwaoka, T; Obatake, N; Aono, J; Hinohara, Y; Nakano, H; et al. (Chugai Pharm. Co. Ltd. Belg. BE 893,553, Chem Abstract 98:215995N Proline Derivatives.

Ryan, J. W., Chung, A. Antihypertensive Mercapto Aczl–Amino Acid Derivatives and Their Use, Chem. Abstract 94:16080C.

McTaggart et al, "The Evaluation of Formulation and Processing Conditions of Melt Granulation Process", *Int. J. of Pharmaceutics*, 19 (1984), pp. 139 to 148.

Shah et al, "Polyethylene Glycol as a Binder for Tablets", *J. of Pharmaceutical Sc.*, vol. 66, No. 11, Nov. 1977, pp. 1551–1552.

Bolhuis et al, "Interaction of Tablet Disintegrants and Magnesium Stearate During Mixing I: Effect on Tablet Disintegration", *J. of Pharmaceut. Sc.*, vol. 70, No. 12, Dec. 1981, pp. 1328–1330.

"Sodium Starch Glycolate", *Explotab*, Edward Mendell Co., Inc. Carmel, N.Y. 10512.

*Primary Examiner*—Stanley J. Friedman
*Attorney, Agent, or Firm*—Browdy and Neimark

[57] ABSTRACT

A stable solid thiol ester derivative preparation which contains as active ingredients a thiol ester derivative or a salt thereof, a water-soluble wax which is solid at ordinary temperatures, and sodium carboxymethyl starch and/or a monovalent electrolyte. Thiol ester derivatives are very useful as drugs but, in a solid state, they are sensitive to moisture. A stable solid preparation of thiol ester derivative is obtained by mixing the above additives and/or a monovalent electrolyte into a thiol ester derivative.

4 Claims, No Drawings

STABLE SOLID PREPARATION OF THIOL ESTER DERIVATIVE

BACKGROUND OF THE INVENTION

The present invention relates to a stable solid preparation of thiol ester derivative that will be very useful as a drug. More particularly, the present invention pertains to a stable solid thiol ester derivative preparation which contains as active ingredients a thiol ester derivative of the formula [I]:

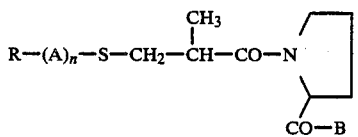

(where R is hydrogen or an acyl group; A is a residue of glycine, sacrosine or α-D-amino acid, the α-carbonyl group of which forms a thiol ester linkage with the sulfur atom; n is an integer 0 or 1; and B is a hydroxyl group or an amino acid residue) or a salt thereof, a water-soluble wax which is solid at ordinary temperatures, and sodium carboxymethyl starch (CMS-Na) and/or a monovalent electrolyte. More specifically, the present invention relates to a stable solid thiol ester derivative preparation which contains as active ingredients a thiol ester derivative of the formula [I]:

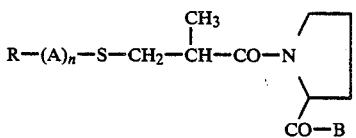

(where R is hydrogen, or an acyl group which is selected from the group consisting of an acetyl, butanecarbonyl, cyclopropanecarbonyl, cyclohexanecarbonyl and adamantanecarbonyl groups and which is linked to an α-amino group of an amino acid of A; A is a residue of glycine, sacrosine or α-D-amino acid, the α-carbonyl group of which forms a thiol ester linkage with the sulfur atom; n is an integer 0 or 1; and B is a hydroxyl group or an amino acid residue) or a salt thereof, a water-soluble wax which is solid at ordinary temperatures, or sodium carboxymethyl starch and/or a monovalent electrolyte.

Thiol ester derivatives represented by the formula [I] have an action suppressing angiotensin converting enzyme.

Thiol ester derivatives which are in a solid state are sensitive to moisture. Therefore, when formulated by an ordinary method, they are affected by water contained in an excipient and by adsorption of moisture in the air, causing decomposition or oxidation, and thus resulting in deterioration of their properties. In order to stabilize such unstable thiol ester derivatives, it is necessary to formulate preparations having water in excipients removed as much as possible and to put them in glass bottles or package them in metallic moistureproof materials. Alternatively, in the case of preparations formulated by an ordinary method, they must be protected by, for example, enclosing a desiccant in their packaging. In these practices, the dehumidification required in formulation and rises in the packaging cost both increase the financial burden on the manufacturer, and it is also troublesome for users to handle and use such preparations.

SUMMARY OF THE INVENTION

The present inventor therefore made various studies in order to obtain a stable solid preparation of thiol ester derivative, and found that a considerably stable solid preparation can be obtained by blending certain additives such as an appropriate wax, a monovalent electrolyte, etc. The present invention has been accomplished on the basis of this finding.

Thus, the present invention provides a stable solid thiol ester derivative preparation obtained in such a manner that one or more water-soluble waxes which are solid at ordinary temperatures are added to and mixed with a thiol ester derivative in an amount from 1% to 50%, preferably from 5% to 30%, and this mixture is heated to a temperature above the melting point of the water-soluble wax(es) to allow the wax to become flowable, and is then stirred so that the wax component is coated on and aggregated with the thiol ester derivative. Then, the aggregate is cooled to obtain a granulated substance, to which is added sodium carboxymethyl starch and/or a monovalent electrolyte in an amount of 0.01% or more, preferably from 0.1% to 20% with respect to the thiol ester derivative.

DETAILED DESCRIPTION OF THE INVENTION

Typical thiol ester derivatives which may be employed in the present invention include N-[3-(N-cyclohexanecarbonyl-D-alanylthio)-2-D-methyl-propanoyl]-L-proline (hereinafter referred to as "compound 1"), N-[3-(N-pivaloyl-D-alanylthio)-2-D-methyl-propanoyl]-L-proline (hereinafter referred to as "compound 2"), D-3-mercapto-2-methlpropanoyl-L-proline (hereinafter referred to as "compound 3") and N-[3-(N-cyclopropanecarbonyl-D-alanylthio)-2-D-methyl-propanoyl]-L-proline (hereinafter referred to as "compound 4"), and also include various salts of these compounds, such as potassium, sodium and lysine salts.

Water-soluble waxes which are solid at ordinary temperatures and which may be employed in the present invention are any waxes having a melting point of 35° C. or higher, preferably from 37° C. to 70° C. Examples include polyethylene glycols, polyethylene propylene glycols, polyethylene nonyl phenol ethers and polyoxyethylene higher alcohol esters. These waxes may be employed alone or mixed together as desired. Heat granulation methods which may be suitably employed in the present invention include generally known granulating methods such as melt granulation, spray granulation, granulation in which a melt is cooled and powdered, fluidized bed granulation and heat granulation by stirring. The feature of these methods resides in that a wax is melted or softened at high temperature, and the ingredients are aggregated by stirring or rolling and then cooled to obtain a granulated substance.

CMS-Na which is employed in the present invention is generally used as a food additive by the name of carboxymethyl starch.

Examples of monovalent electrolytes which may be employed in the present invention include sodium chloride, potassium chloride, sodium bromide, lithium chloride and sodium nitrate, and these electrolytes may be mixed together when added to the selected thiol ester derivative.

Excipients which may appropriately be employed in formulation include lactose, corn starch, potato starch, crystalline cellulose, mannitol, calcium citrate and calcium hydrogenphosphate.

Solid preparations obtained in accordance with the present invention have excellent stability.

The following examples are provided for the purpose of further illustrating the present invention but are not to be construed as limiting. It should be noted that "parts" in the following examples denote parts by weight.

EXAMPLE 1

Twenty parts of polyethylene glycol-6000 was added to and mixed with 80 parts of crystalline powder of the calcium salt of compound 1, and the mixture was then granulated by heating to obtain a granulated substance. Ten parts of CMS-Na was added to and mixed with 90 parts of the obtained granulated substance, and the mixture was then subjected to an ordinary tablet making process to obtain tablets.

EXAMPLE 2

Five parts of CMS-Na was added to and mixed with 95 parts of a granulated substance obtained from the compound 3 in the same way as in Example 1, and the mixture was then subjected to an ordinary tablet making process to obtain tablets.

EXAMPLE 3

Twenty parts of CMS-Na was added to and mixed with 80 parts of a granulated substance obtained in the same way as in Example 1, and the mixture was then subjected to an ordinary tablet making process to obtain tablets.

EXAMPLE 4

Ten parts of CMS-Na was added to and mixed with 90 parts of a granulated substance obtained in the same way as in Example 1, and the mixture was then charged into hard capsules by an ordinary method to obtain capsulated preparations.

EXAMPLE 5

The calcium salt of the compound 2 was processed in the same way as in Example 1 to obtain tablets.

EXAMPLE 6

The compound 4 was processed in the same way as in Example 1 to obtain tablets.

EXAMPLE 7

Twenty parts of polyethylene glycol-6000 was added to and mixed with 80 parts of crystalline powder of the calcium salt of the compound 1. The mixture was then granulated by heating to obtain a granulated substance. Nine parts of corn starch and one part of sodium chloride were added to and mixed with 90 parts of the obtained granulated substance, and the mixture was then subjected to an ordinary tablet making process to obtain tablets.

EXAMPLE 8

Nine parts of corn starch and one part of potassium chloride were added to and mixed with 90 parts of a granulated substance obtained in the same way as in Example 7, and the mixture was then subjected to an ordinary tablet making process to obtain tablets.

EXAMPLE 9

Nine parts of corn starch and one part of sodium bromide were added to and mixed with 90 parts of a granulated substance obtained in the same way as in Example 7, and the mixture was then subjected to an ordinary tablet making process to obtain tablets.

EXAMPLE 10

Nine parts of corn starch and one part of sodium nitrate were added to and mixed with 90 parts of a granulated substance obtained in the same way as in Example 7, and the mixture was then subjected to an ordinary tablet making process to obtain tablets.

EXAMPLE 11

Twenty parts of polyethylene glycol-6000 was added to and mixed with 80 parts of crystalline powder of the calcium salt of compound 3. The mixture was then granulated by heating to obtain a granulated substance, and 9.9 parts of corn starch and 0.1 part of sodium chloride were added to and mixed with 90 parts of the obtained granulated substance. The mixture was then subjected to an ordinary tablet making process to obtain tablets.

EXAMPLE 12

Twenty parts of polyethylene polypropylene glycol was added to and mixed with 80 parts of crystalline powder of the calcium salt of compound 2, and the mixture was then granulated by heating to obtain a granulated substance. Nine parts of corn starch and one part of sodium chloride were added to and mixed with 90 parts of the obtained granulated substance, and the mixture was then subjected to an ordinary tablet making process to obtain tablets.

EXAMPLE 13

Twenty parts of polyethylene glycol-6000 was added to and mixed with 80 parts of crystalline powder of the calcium salt of compound 4, and the mixture was then granulated by heating to obtain a granulated substance. Nine parts of microcrystalline cellulose and one part of sodium chloride were added to and mixed with 90 parts of the obtained granulated substance, and the mixture was then subjected to an ordinary tablet making process to obtain tablets.

EXAMPLE 14

Nine parts of corn starch and one part of potassium chloride were added to and mixed with 90 parts of a granulated substance obtained in the same way as in Example 7, and the mixture was then charged into hard capsules by an ordinary method to obtain capsulated preparations.

EXAMPLE 15

Twenty parts of polyethylene glycol-6000 was added to and mixed with 80 parts of crystalline powder of the calcium salt of compound 1. The mixture was then granulated by heating to obtain a granulated substance, and 9.5 parts of CMS-Na and 0.5 parts of sodium chloride were added to and mixed with 90 parts of the obtained granulated substance. The mixture was then subjected to an ordinary tablet making process to obtain tablets.

EXAMPLE 16

Nineteen parts of mannitol, 0.5 parts of sodium chloride and 0.5 parts of potassium chloride were added to and mixed with 80 parts of a granulated substance obtained in the same way as in Example 15, and the mixture was then subjected to an ordinary tablet making process to obtain tablets.

COMPARATIVE EXAMPLE 1

Ten parts of corn starch was added to and mixed with 90 parts of a granulated substance obtained in the same way as in Example 1, and tablets were obtained in the same way as in Example 1.

COMPARATIVE EXAMPLEe 2

Fifty parts of lactose and 30 parts of microcrystalline cellulose were added to and mixed with 20 parts of calcium salt of the compound 1, and the mixture was then subjected to an ordinary tablet making process to obtain tablets.

COMPARATIVE EXAMPLE 3

A powder mixture obtained in the same way as in Comparative Example 2 was charged into hard capsules by an ordinary method to obtain capsulated preparations.

COMPARATIVE EXAMPLE 4

Ten parts of corn starch was added to and mixed with 90 parts of a granulated substance obtained in the same way as in Example 5, and tablets were obtained in the same way as in Example 5.

COMPARATIVE EXAMPLE 5

Ten parts of corn starch was added to and mixed with 90 parts of a granulated substance obtained in the same way as in Example 6, and tablets were obtained in the same way as in Example 6.

COMPARATIVE EXAMPLE 6

Ten parts of corn starch was added to and mixed with 90 parts of a granulated substance obtained in the same way as in Example 7, and tablets were obtained in the same way as in Example 7.

COMPARATIVE EXAMPLE 7

Forty parts of lactose and 20 parts of microcrystalline cellulose were added to and mixed with 40 parts of the calcium salt of compound 1, and the mixture was then subjected to an ordinary tablet making process to obtain tablets.

COMPARATIVE EXAMPLE 8

Ten parts of corn starch was added to and mixed with 90 parts of a granulated substance obtained in the same way as in Example 11, and tablets were obtained in the same way as in Example 11.

COMPARATIVE EXAMPLE 9

Ten parts of corn starch was added to and mixed with 90 parts of a granulated substance obtained in the same way as in Example 12, and tablets were obtained in the same way as in Example 12.

COMPARATIVE EXAMPLE 10

Ten parts of corn starch was added to and mixed with 90 parts of a granulated substance obtained in the same way as in Example 13, and tablets were obtained in the same way as in Example 13.

COMPARATIVE EXAMPLE 11

Ten parts of corn starch was added to and mixed with 90 parts of a granulated substance obtained in the same way as in Example 7, and the mixture was then charged into hard capsules by an ordinary method to obtain capsulated preparations.

EXPERIMENTAL EXAMPLE

A stability test was carried out on the preparation samples shown in the Examples and Comparative Examples under the following conditions. Six grams of each sample was put in a glass bottle and, with the bottle opened, it was stored in a desiccator at 50° C.-75% RH (relative humidity). After 30 days or 60 days had passed, the residual amount of the principal ingredient in the sample was measured by highspeed liquid chromatography. The results are shown in Tables 1 and 2 below.

TABLE 1

| Samples | Residual Principal Ingredients (%) 50° C. - 75% RH | |
|---|---|---|
| | 30 days | 60 days |
| Example | | |
| 1 | 98.9 | 91.2 |
| 2 | 97.6 | 91.3 |
| 3 | 98.8 | 92.5 |
| 4 | 98.5 | 97.1 |
| 5 | 98.2 | 90.3 |
| 6 | 99.3 | 93.6 |
| 7 | 98.5 | 94.8 |
| 8 | 97.1 | 91.2 |
| 9 | 98.7 | 93.8 |
| 10 | 95.0 | 88.5 |
| 11 | 97.4 | 92.8 |
| 12 | 98.1 | 91.3 |
| 13 | 99.1 | 93.7 |
| 14 | 99.0 | 96.6 |
| 15 | 98.5 | 97.6 |
| 16 | 97.3 | 96.0 |

TABLE 2

| Samples | Residual Principal Ingredients (%) 50° C. - 75% RH | |
|---|---|---|
| | 30 days | 60 days |
| Comparative Example | | |
| 1 | 86.8 | 61.3 |
| 2 | 87.3 | 72.9 |
| 3 | 85.3 | 66.4 |
| 4 | 90.5 | 74.3 |
| 5 | 92.4 | 77.8 |
| 6 | 85.9 | 58.3 |
| 7 | 88.3 | 74.2 |
| 8 | 84.9 | 63.2 |
| 9 | 90.1 | 73.6 |
| 10 | 92.7 | 78.3 |
| 11 | 85.1 | 69.5 |

I claim:

1. A stable solid thiol ester derivative preparation which contains as an active ingredient a therapeutically effective amount of thiol ester derivative of the formula I or a salt thereof:

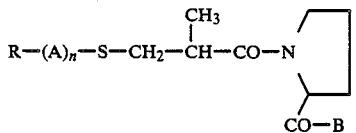

wherein R is hydrogen or any acyl group; A is a residue of glycine, sacrosine or alpha-D-amino acid, the alpha-carbonyl group of which forms a thiol ester linkage with the sulfur atom; n is an integer 0 or 1; and B is a hydroxyl group or an amino acid residue;

a water-soluble wax selected from the group consisting of a polyethylene glycol, a polyethylene propylene glycol, a polyethylene nonyl phenol ether and a polyoxyethylene higher alcohol ester in an amount of 1–50% by weight;

and a substance selected from the group consisting of sodium carboxymethyl starch, sodium chloride, potassium chloride, sodium bromide, lithium chloride and sodium nitrate, or mixtures thereof in an amount of at least 0.01% by weight.

2. A stable solid thiol ester derivative preparation according to claim 1, wherein said acyl group is selected from the group consisting of acetyl, butanecarbonyl, cyclopropanecarbonyl, cyclohexanecarbonyl and adamantanecarbonyl groups and R is linked to an alpha-amino group of A.

3. The preparation of claim 1, wherein said substance is present in an amount of 0.1–20% by weight.

4. The preparation of claim 1, wherein said wax is present in an amount of 5–30% by weight.

* * * * *